United States Patent [19]

Polansky et al.

[11] Patent Number: 5,474,985
[45] Date of Patent: Dec. 12, 1995

[54] PREVENTING AND TREATING ELEVATED INTRAOCULAR PRESSURE ASSOCIATED WITH ADMINISTERED OR ENDOGENOUS STEROIDS USING NON-STEROIDAL CYCLOOXYGENASE INHIBITORS

[75] Inventors: Jon R. Polansky, Mill Valley; Ernest Bloom, Alamo; Donald J. Fauss, San Francisco, all of Calif.

[73] Assignee: The Regents of the University of California, Oakland, Calif.

[21] Appl. No.: 171,448

[22] Filed: Dec. 22, 1993

[51] Int. Cl.⁶ .................. A61K 31/19; A61K 31/405; A61K 31/195
[52] U.S. Cl. .................. 514/26; 514/912; 514/913; 514/914; 514/964; 424/468; 424/497; 424/78.04; 424/78.05
[58] Field of Search .................. 424/468, 497, 424/78.04, 78.05; 514/912, 913, 914, 964, 26

[56] References Cited

U.S. PATENT DOCUMENTS

| | | | |
|---|---|---|---|
| 3,732,865 | 5/1973 | Higuchi et al. | 128/127 |
| 4,192,827 | 3/1980 | Mueller | 525/123 |
| 4,327,725 | 5/1982 | Cortese et al. | 424/468 |
| 4,454,151 | 6/1984 | Waterbury | 514/912 |
| 4,522,826 | 6/1985 | Sunshine et al. | 514/569 |
| 4,543,251 | 9/1985 | Kamishita | 424/81 |
| 4,548,990 | 10/1985 | Mueller et al. | 525/123 |
| 4,670,254 | 6/1987 | Kamishita | 424/81 |
| 4,690,927 | 9/1987 | Voss et al. | 514/282 |
| 4,711,782 | 12/1987 | Okada et al. | 424/455 |
| 4,711,906 | 12/1987 | von Stetten et al. | 514/561 |
| 4,757,060 | 7/1988 | Lukacsko et al. | 514/160 |
| 4,777,174 | 10/1988 | Sunshine et al. | 514/264 |
| 4,829,088 | 5/1989 | Doulakas | 514/567 |
| 4,855,293 | 8/1989 | Collington et al. | 514/212 |
| 4,876,250 | 10/1989 | Clark | 514/172 |
| 4,880,742 | 11/1989 | Hayaishi et al. | 435/238 |
| 4,904,649 | 2/1990 | Schwartz | 514/174 |
| 4,917,886 | 4/1990 | Asche et al. | 424/81 |
| 4,948,805 | 8/1990 | Ziggiotti et al. | 514/428 |
| 4,960,799 | 10/1990 | Nagy | 514/567 |
| 4,971,802 | 11/1990 | Tarcsay et al. | 424/450 |
| 4,973,469 | 11/1990 | Mulligan et al. | 424/461 |
| 4,980,170 | 12/1990 | Schneider et al. | 424/451 |
| 4,999,379 | 3/1991 | Fankhauser | 514/567 |
| 5,036,097 | 7/1991 | Floyd et al. | 514/400 |
| 5,110,493 | 5/1992 | Cherng-Chyi et al. | 514/413 |
| 5,124,154 | 6/1992 | Babcock et al. | 424/427 |
| 5,314,909 | 5/1994 | Dollerup | 514/419 |

FOREIGN PATENT DOCUMENTS

| | | |
|---|---|---|
| 0160408 | 11/1985 | European Pat. Off. . |
| 0390071A1 | 10/1990 | European Pat. Off. . |
| 0422681 | 4/1991 | European Pat. Off. . |
| 0422681A1 | 4/1991 | European Pat. Off. . |
| 0466650A2 | 1/1992 | European Pat. Off. . |
| WO89/06964 | 8/1989 | WIPO . |
| WO91/16896 | 11/1991 | WIPO . |
| WO91/19482 | 12/1991 | WIPO . |
| WO92/00044 | 1/1992 | WIPO . |
| WO92/00707 | 1/1992 | WIPO . |

OTHER PUBLICATIONS

Huk, et al: Ophthalmologica, vol. 203, No. 1, 1991 (pp. 24–29)–"Anti–Inflammatory Treatment after Argon Laser Trabeculoplasty".
Icy Hot® distributed by Chattem Consumer Products.
Rite Aid Muscle Rub® distributed by Rite Aid.
Zambon Group (Bonadeo et al): Derwent Publications Ltd., London, GB (AN 93–220718)–Jul. 1993 Abstract.
Patent Abstracts of Japan, vol. 011, No. 349 (C–456) (Nov. 14, 1987) & JP A 62 123 119 (The Green Cross Corp.)–Jun. 4, 1987.
Weinreb et al: Investigative Ophthalmology & Visual Science, Dec. 1983 vol. 24/12–"Prostaglandin Production by Human Trabecular Cells": In Vitro Inhibition by Dexamethasone.
Klaus Trier, Elith Bjarne Olsen, "*The Use of Estrogens in the Preparation of Formulations for Topical Treatment of High Pressure in the Eyes*", 1992, Chemical Abstracts, vol. 117, p. 480.
J. R. Polansky, R. M. Kurtz, D. J. Fauss, R. Y. Kim and E. Bloom, "*In Vitro Correlates of Glucocorticoid Effects of Intraocular Pressure*", G. K. Krieglstein(Ed.), Glaucoma Update IV, 1991, pp. 20–29.
Allan J. Flach, M.D., Pharm. D., "*Cyclo–oxygenase Inhibitors in Ophthalmology*", Survey of Ophthalmology, vol. 36, No. 4, Jan.–Feb. 1992, pp. 259–284.
Jon R. Polansky, Ron M. Kurtz, Jorge A. Alvarado, Robert N. Weinreb, and Murray D. Mitchell, "*Eicosanoid Production and Glucocorticoid Regulatory Mechanisms in Cultured Human Trabecular Meshwork Cells*", Cellular Pharmacology Laboratory, University of California, The Oailor Effects of Prostaglandins and Other Eicosanoids, pp. 113–138 (1989) Alan R. Liss, Inc.
J. R. Polansky and R. N. Weinreb, "Anti–Inflammatory Agents: Steroids as *Anti–Inflammatory Agents*", Handbook of Experimental Pharmacology, vol. 69, pp. 491–503 (1984).
Jon Polansky, Paul Palmberg, Daniel Matulich, Nancy Lan, Shirley Hajek, Anthony Hajek, Bernard Becker and John Baxter, "*Cellular Sensitivity to Glucocorticoids in Patients with POAG*", Investigative Ophthalmology & Visual Science, vol. 26, No. 6, Jun. 1985, pp. 805–809.
John D. Mullins, Ph.D., Gerald Hecht, Ph.D. "*Ophthalmic Preparations*" Chapter 86, Remington's Pharmaceutical Sciences, 18th Ed., pp. 1581–1595 (1990).

(List continued on next page.)

*Primary Examiner*—Ronald W. Griffin
*Attorney, Agent, or Firm*—Howrey & Simon

[57] ABSTRACT

Methods and compositions for preventing or treating non-inflammatory elevated intraocular pressure associated with administered or endogenous steroids including administering to a mammalian organism a composition including (a) an ophthalmologically effective amount of a non-steroidal cyclooxygenase inhibitor, and (b) a pharmaceutically acceptable carrier, to reduce or prevent an elevation of intraocular pressure and/or protein marker induction induced by chronic exposure to glucocorticoids.

74 Claims, No Drawings

OTHER PUBLICATIONS

Jack Hartstein, "*Glaucoma*", McGraw–Hill Encyclopedia of Science & Technology, 6th Ed., pp. 131–132 (1987).

Jack Hartstein, "*Eye (vertebrate)*", McGraw–Hill Encyclopedia of Science & Technology, 6th Ed., pp. 544–552 (1987).

Paul A. Insel, "*Analgesic–Antipyretics and Antiinflammatory Agents; Drugs Employed in the Treatment of Rheumatoid Arthritis and Gout*", Goodman and Gilman's The Pharmacological Basis of Therapeutics, 8th Ed., Chapter 26, pp. 638–641 (1990).

David L. Epstein, M.D., "*Glaucoma*", Chandler and Grant's 3rd Edition, pp. 3–5, 129–143, 181–183, 191, 194–195, 201–211, 293–294, 311, 320–321, 352–379, 396 and 403–407 (1986).

Jon R. Polansky, Md, "*Side Effects of Topical Ophthalmic Therapy With Anti–Inflammatory Steroids and β–Blockers*", Current Opinion in Ophthalmology, vol. 3, 1992, pp. 259–272.

Jon R. Polansky, E. Bloom, G. M. Lui, A. Baur and D. J. Fauss, "*Growth Factor Effects and Modulation of Glucocorticoid (GC) and Other Stress Responses in Human Trabecular Meshwork (HTM) Cells*", Experimental Eye Research, vol. 55, Suppl. 1, Sep. 1992.

Jon R. Polansky, MD, "*Basics Pharmacology of Corticosteroids*", Current Topics in Ocular Inflammation, No. 1, 1993, pp. 9–21.

Jon R. Polansky, "*HTM Cell Culture Model For Steroid Effects on Intraocular Pressure: Overview*", Basic Aspects of Glaucoma Research III, Sep. 23–25, 1991, pp. 307–343.

PREVENTING AND TREATING ELEVATED INTRAOCULAR PRESSURE ASSOCIATED WITH ADMINISTERED OR ENDOGENOUS STEROIDS USING NON-STEROIDAL CYCLOOXYGENASE INHIBITORS

ACKNOWLEDGEMENT OF GOVERNMENT SUPPORT

This invention was made with Government support under Grant Nos. EY-02477 and EY-08973, awarded by the National Institute of Health. The Government has certain rights in this invention.

FIELD OF THE INVENTION

This invention relates to methods for the prevention and treatment of elevated intraocular pressure which is a factor involved in developing optic nerve damage and loss of vision. More particularly, this invention relates to new methods for treating the eye with non-steroidal cyclooxygenase inhibitors (or non-steroidal anti-inflammatory, NSAI, agents) to prevent or treat elevated intraocular pressure due to administered or endogenous steroids (glucocorticoids).

BACKGROUND OF THE INVENTION

Glucocorticoids (also known as anti-inflammatory corticosteroids, corticosteroids, or simply as "steroids" in the ophthalmic literature) have been known since the early 1950's as effective therapeutic agents for reducing ocular inflammation. The introduction of anti-inflammatory steroid therapy, using a variety of local and systemic routes of delivery, continues to provide a means to decrease the inflammation which otherwise would damage and impair the vision of the patient. Ophthalmic steroid therapy proved useful to a wide variety of inflammatory and irritating conditions in the eye where other therapies either did not work as well or were ineffective. Steroids were not useful for many other conditions, especially chronic ones in which inflammatory mechanisms did not play a clear pathogenic role (including cataract, most forms of glaucoma, and macular degeneration).

As ophthalmic steroid therapy became more widespread, and more potent and stable steroids became available, it became clear that their use involved a number of potential side-effects, one of the first of which noticed was elevation of pressure within the eye (intraocular pressure [IOP]). Concern over this side-effect has become a limitation on the long-term ophthalmic use of both potent and less active steroids, especially because a number of cases were reported in which irreversible blindness has occurred due to unrecognized increased IOP.

When detailed evaluations of the potent ophthalmic steroid formulations was conducted in large populations using standardized testing protocols (four times a day administration of ophthalmic 0.1% dexamethasone eyedrops), it was determined that elevated IOP occurred relatively frequently in the general population within three to six weeks. Potentially serious elevations in IOP occurred in some patients within the first week of ophthalmic steroid administration. The longer the duration and the more frequent the steroid administration, the more likely a given patient was shown to develop elevated IOP. Approximately 5 percent of the general population show an accentuated IOP elevation to topical ophthalmic steroids (in which IOP can increase from its normal 10 to 20 mm Hg to over 35 mm Hg) occurring in the one-to-six week time frame of steroid administration. Some patients who did not show a nigh response to the normal steroid eyedrop testing protocol did show a large IOP rise with longer treatments and/or different routes (e.g. injectable steroids) of steroid administration. If undetected, such high elevations of IOP (as well as elevations in the range of 20 to 30 mm Hg) were known to put the patient at substantial risk of glaucomatous damage as evidenced by loss of vision in visual field testing and optic nerve damage. Even minor increases in IOP can be detrimental in some patients such as those with low-tension glaucoma.

Elevated IOP is currently recognized as an important risk factor for the development of optic nerve damage and visual field loss in otherwise normal individuals. The concern is even greater for patients who are already demonstrating such damage due to glaucoma. Individuals with primary open-angle glaucoma (POAG), also called "chronic glaucoma", which is the most prevalent type of glaucoma, have additional problems with ophthalmic steroid therapy in that these patients (and their genetically related family members) appear predisposed to high IOP elevations due to steroids. Patients with pigmentary glaucoma also appear to have an increased sensitivity to steroid administration, while other forms of glaucoma do not appear to have this increased sensitivity.

In addition to direct ophthalmic steroid use, dermatologic steroids used on the face and eyelids are sufficient to produce elevated IOP and visual loss in some individuals. Elevated IOP occurs also with systemic steroid use, increased endogenous steroids as occurs with Cushing's Syndrome, and POAG itself may involve an increased activity or response to excessive endogenous glucocorticoid activity.

Efforts have been made to substitute non-steroidal anti-inflammatory (NSAI) agents, from the group of drugs known as cyclooxygenase inhibitors (a number of which were known useful in treating systemic inflammatory medical conditions), for the use of steroids in the treatment of ocular inflammation and ocular pain syndromes. These agents have not shown the same propensity to produce side-effects in ocular tissues as do ophthalmic steroids (in addition to the IOP rise, steroid side effects include steroid cataract, delayed wound healing, and the masking or spreading of infections), although a concern has remained that NSAI agents might elevate IOP or produce other steroid-related complications in the eye since their accepted mechanism of action is to inhibit the production of prostaglandins and other eicosanoids similar to steroids. Because prostaglandin administration does appear to decrease IOP and to increase outflow, blockage of endogenous prostagladins by steroid (or NSAI agents) in trabecular meshwork cells from the aqueous outflow pathway could contribute to a rise in IOP. See, e.g., Weinreb et al., Arachidonic Acid Metabolism in HTM Cells, Investigative Ophthalmology & Visual Science, Vol. 29, No. 11 (1988) and Weinreb et al., Prostaglandin Production by HTM Cells: In Vitro Inhibition by Dexamethasone, Investigative Ophthalmology & Visual Science, Vol. 24, No. 12 (1983).

Doulakas (U.S. Pat. No. 4,829,088) discloses the use of an ophthalmic medicament containing diclofenac-sodium in aqueous solution for the treatment of inflammations of the eye. Diclofenac-sodium is a non-steroidal anti-inflammatory agent which is said to be a suitable alternative for the treatment of severe acute or chronically recurrent inflammatory symptoms in the eye. The aqueous solution is made suitable for the local treatment of inflammations of the eye due to its stability against chemical decomposition of the diclofenac-sodium and preservation properties and toleration by the eye.

Nagy (U.S. Pat. No. 4,960,799) also discloses aqueous ophthalmic solutions containing diclofenac-sodium. The solutions, having a pH of about 7.0 to about 7.8, comprise per milliliter of solution about 0.1 to about 5.0 milligrams of (a) pharmaceutically acceptable salt of ortho-(2,6-dichlophenyl-)aminophenyl acetic acid; (b) about 0.1 to about 10 milligrams of a pharmaceutically acceptable salt of ethylene diamine tetraacetic acid, (c) about 0.5 to about 200 milligrams of a pharmaceutically acceptable solubilizer, (d) about 0.01 to about 5.0 milligrams of a pharmaceutically acceptable bacteriostat and (e) the remainder water. The ophthalmic solutions are used for topical administration to the eye for the control or treatment of ocular inflammation.

Cherng-Chyi et al. (U.S. Pat. No. 5,110,493) relates to ophthalmic non-steroidal anti-inflammatory drug formulations containing a quaternary ammonium preservative and a non-ionic surfactant. The formulations are useful for treating diseases that are either caused by, associated with or accompanied by inflammatory processes.

The NSAI agents used in the eye have been tested empirically for different ocular inflammatory conditions, using drugs that had been selected previously in systemic studies for their ability to suppress prostaglandin production and to decrease inflammatory responses in animals and humans. In the eye, these NSAI agents appear to provide at least some benefit to prevent particular side-effects of surgical trauma, fluid accumulating in the back of the eye, appearance of inflammatory cells and vessel leakage in the anterior chamber, and the presence of pain. Although potentially useful to these conditions and ocular disease states, and some ocular conditions such as post surgical macular edema appear to respond better to some NSAIs than steroid administration, NSAI agents do not appear as fully-effective alternatives for steroid treatment of ocular inflammation in many other conditions, and in a variety of individual clinical settings ophthalmic steroid therapy is still preferred.

As mentioned earlier, steroids (glucocorticoids) are believed to alleviate inflammation at least in part by inhibiting the production of prostaglandins and other eicosanoids at early stage involving the utilization of arachidonic acid (by interactions with lipomodulin-like molecules), although it is clear that other steroid actions also contribute to their antiinflammatory effects. NSAIs also are believed to inhibit the formation of prostaglandins and other eicosanoids at a later step (by interaction with the enzyme cyclooxygenase) as the major mechanism for their antiinflammatory effects. However, since steroids and NSAI agents both effectively inhibit prostaglandin and other eicosanoid pathways, a concern has been that both classes of drugs might elevate IOP.

SUMMARY AND OBJECTS OF THE INVENTION

It is a primary objective of the present invention to provide novel methods and compositions for decreasing the propensity of steroids (glucocorticoids) to produce IOP elevation.

Yet another object of the present invention is to provide novel methods and compositions capable of preventing or ameliorating particular eye diseases such as primary open-angle glaucoma and pigmentary glaucoma whose conditions are associated with an increased propensity for steroid-induced IOP elevation (and whose pathogeneses may involve endogenous glucocorticoids).

Still other objects of the present invention are to provide novel methods which employ NSAI (cyclooxygenase inhibitors) to prevent or treat elevated IOP induced by glucocorticoids also termed steroids.

With regard to the above, certain NSAI agents show quite unexpected activities to block the appearance of major protein markers for steroid effects on IOP using human trabecular meshwork (termed HTM) cells exposed to the potent glucocorticoid dexamethasone. Such agents for this reason represent useful therapeutic agents for treating certain chronic, non-inflammatory forms of glaucoma such as POAG and pigmentary glaucoma. Since certain NSAI agents were shown to help alleviate glucocorticoid inductions in cultured HTM cells, both in the cell layer and in the media surrounding the cells (based on their mobilities on SDS-gel electrophoresis these major glucocorticoid inductions have been termed herein "55 kDa" and "66 kDa" protein/glycoprotein marker inductions, although they appear in a range of about 52–56 kDa and about 64–70 kDa, in the cell and in the media, respectfully). These proteins have dose response and time course characteristics that set them apart from most of the other glucocorticoid regulated proteins in HTM cells, and these characteristics correspond to those observed for steroid induced IOP changes in human subjects. For this reason, these proteins have been identified as "markers" for the glucocorticoid induced response of HTM cells related to IOP changes. Since the 55 kDa protein in the HTM cell layer is rapidly secreted into the media in a glycosylated form (i.e., the 66 kDa protein), and since the 66 kDa protein is readily separated from other background proteins detected using labeled amino-acid protein precursors, this marker was preferred to evaluate the ability of drugs to block glucocorticoid induced effects on the cells related to IOP changes. The NSAI agents may also help the HTM cells to function more normally and preserve themselves, i.e., maintain their normal extracellular environment, as well as their shape and cell number, when exposed to glucocorticoids.

The above findings were quite unexpected since inhibition of prostaglandins by NSAI agents would add to the inhibition of prostaglandins by glucocorticoids in HTM cells. Such inhibition by cyclooxygenase inhibitors of these pathways would not be expected to produce beneficial effects. In this regard, the NSAIs as non-steroidal eicosanoid inhibiting agents of the present invention were believed to further inhibit pathways needed to maintain normal outflow pathways and IOP. Thus, the effective use of such agents to ameliorate elevated IOP induced by steroid treatment is not expected.

In one aspect, the present invention involves methods of arresting processes causing damage to the eye of a human or other animal that is subject to intraocular damage and in need of maintaining visual function or prevention of its loss from such damage, wherein certain non-steroidal cyclooxygenase inhibitors or NSAI agents which function as therapeutic agents are administered in an inert vehicle to eye tissue by intraocular injection or topically. The term "inert vehicle" is broadly used herein to optionally include adjuvants, preservatives, buffers, demulcents and anything else that is essentially inert relative to the therapeutic function of the non-steroidal cyclooxygenase inhibitors or NSAI agents.

In another aspect, the present invention involves methods of preventing or treating ophthalmic diseases or disorders in a human or other animal that is subject to intraocular damage and in need of improved visual function or prevention of its loss from such damage, wherein an ophthalmologically effective amount of certain non-steroidal cyclooxygenase inhibitors or NSAI agents which function as a therapeutic agent are administered, in an inert vehicle, to arrest processes, and particularly, those processes induced by steroids which are damaging to the eye. As used herein, "ophthalmically effective amount" is that amount which, in the composition administered and by the technique administered, provides an amount of therapeutic agent to the involved eye tissues sufficient to reduce intraocular pressure or prevent its rise associated with steroid treatments.

The present invention also involves methods of arresting processes causing damage to the eye, wherein certain non-steroidal cyclooxygenase inhibitors or NSAI agents which function as therapeutic agents are administered topically. When the administration is topical (either dermal or topically ophthalmic), a topical formulation containing between 0.001 and 10%, preferably between 0.05 and 1%, and more preferably between 0.05 and 0.6% by weight; and preferably it is administered as a topical ophthalmic formulation in an aqueous polymeric solution, aqueous suspension, ointment, or gel vehicle. In other preferred topical formulations, between 0.001 and 0.009% by weight of the agent is employed. Except for ointments, these vehicles may contain liposomes for creating a reservoir of dissolved agent for contact with the tear film.

The present invention also involves methods of arresting processes causing damage to the eye, wherein certain NSAI agents or non-steroidal cyclooxygenase inhibitors which function as therapeutic agents are administered by intraocular injection. When the intraocular injection is subconjunctival, a formulation containing between 0,001 and 5%, preferably between 0.01 and 1.0%, by weight of the therapeutic agent is administered; and preferably it is administered in a polymeric carrier such as methylcellulose polycarbophil, hydroxymethylcellulose or dextran, with the formulations containing additives such as disodium edetate, sodium sulfite, and/or sodium chloride, and sodium hydroxide or hydrogen chloride for pH adjustment. When the intraocular injection is intracameral or intravitreal, a formulation containing between 0.001 and 1%, preferably between 0.01 and 1.0% especially when in solution, by weight of the therapeutic agent is administered; and preferably it is administered in a vehicle containing phosphate buffered saline, citrate buffered saline, or chondroitin sulfate, or in a polymeric vehicle such as sodium hyaluronate, or hyaluronic acid, purified polyacrylamide or polysorbate 80, with the formulation containing sodium hydroxide or hydrogen chloride for pH adjustment.

The present invention also involves methods of arresting processes causing damage to the eye, wherein certain non-steroidal cyclooxygenase inhibitors or NSAI agents which function as therapeutic agents are administered systemically. One such systemic administration is by intramuscular injection. Such formulations may contain between 0.01 and 10%, preferably between 0.5 and 5%, by weight of the therapeutic agent, preferably in a polysorbate 80, methyl cellulose, or other polymeric vehicle.

Another such systemic administration is by oral dosage. When administered orally in an aqueous solution, aqueous suspension, elixir or other liquid, formulations containing between 0.1 and 50%, preferably between 1.0 and 10%, by weight of the therapeutic agent may be employed. When administered orally as a solid, tablets, caplets or capsules containing between 1 and 1000 mg of the therapeutic agent may be employed.

Another such systemic administration is by intravenous injection. When administered intravenously, formulations containing between 0.05 and 5%, preferably between 0.1 and 1% by weight, of the therapeutic agent is employed, preferably in a citrate buffer or borate buffer carrier or in a lipid emulsion, unilamellar liposome or multilamellar liposome formulation.

In a further aspect, the present invention involves a composition for preventing or treating ophthalmic diseases or disorders, comprising: (a) a selected non-steroidal cyclooxygenase inhibiting therapeutic agent or NSAI agent, and (b) an inert ophthalmic vehicle, suitable for a topical, preferably topically ophthalmic, systemic or intraocular application, selected from polymeric solutions, suspensions, ointments or gels. The aqueous carriers may contain liposomes for creating a reservoir of dissolved agents for contact with the tear film. Gels for topical ophthalmic applications are the most preferred carriers. The composition contains an ophthalmically effective amount of an cyclooxygenase inhibiting agent or NSAI agent to arrest processes damaging to the eye resulting from increased intraocular pressure associated with steroid treatment.

In another aspect of the invention, there is a novel ointment, gel or drop ophthalmic composition containing an amount of NSAI less than or equal to that typically required to reduce inflammation. Such composition includes a cyclooxygenase inhibiting agent and or NSAI agent and an inert carrier suitable for application to the eye. Preferably, the composition contains 0.001 to 0.009, preferably 0.005 to 0.008 percent by weight cyclooxygenase inhibiting agent.

Advantageously, the cyclooxygenase inhibiting agents or NSAI agents may be administered chronically or acutely, while preventing tissue damage and minimizing any acute injury and preventing the onset of the diseased state.

With the foregoing as well as other objects, advantages, features and aspects of the invention that will become hereinafter apparent, the nature of the invention may be more clearly understood by reference to the detailed description of the invention and to the appended claims.

DETAILED DESCRIPTION OF PREFERRED EMBODIMENTS

The present invention encompasses methods and compositions for preventing or treating an ophthalmic disease or disorder, wherein an ophthalmically effective amount of a non-steroidal cyclooxygenase inhibiting, or non-steroidal anti-inflammatory (NSAI) therapeutic agent, and an inert ophthalmic vehicle, are administered to prevent onset of or reduce abnormally high IOP associated with treatment with steroids, corticosteroids or glucocorticoids. The steroids, corticosteroids or glucocorticoids may be used as a treatment of an ocular or other condition such as inflammation or naturally produced by the organism treated, i.e., Cushing syndrome.

Non-steroidal anti-inflammatory agents are widely prescribed to reduce pain and inflammation in a wide number of tissues. This includes their application as topical agents in the eye, in which their ability to suppress inflammatory responses and to prevent particular side-effects of surgical trauma (on the pupil preventing surgical meiosis), fluid accumulating in the back of the eye after cataract surgery (post-surgical macular edema) and the appearance of inflammatory cells and vessel leakage in the anterior chamber. Topical application of NSAI agents in the eye also appear to relieve some of the itching due to allergic conjunctivitis. These conditions fit in the normal and expected effects of NSAI agents in inflammation and pain.

The present invention, however, relates to new methods of treatment and compositions for relieving or arresting processes which induce elevated IOP associated with steroid use. While not wishing to be bound by theory, steroid elevations of IOP appear to be due to an increased resistance in the trabecular meshwork pathway, the major pathway through which aqueous humor fluid produced by the ciliary body must flow.

The invention also includes treatment of types of glaucoma such as steroidal glaucoma and POAG and pigmentary glaucoma which are not thought to involve inflammation as a pathogenic mechanism. Thus, the present invention relates to prevention and treatment of elevated IOP associated with steroid or glucocorticoid treatment.

Prior to discussing examples of the invention, a brief discussion is provided concerning non-steroidal cyclooxygenase inhibiting agents. As used herein, "cyclooxygenase inhibiting agents" include those compounds which inhibit prostaglandin and other eicosanoid or cyclooxygenase pathways which are believed to affect IOP. Compounds considered within the classification of cyclooxygenase inhibitors include certain NSAI agents.

NSAI agents have been documented by J. Lombardino in "Nonsteroidal Antiinflammatory Drugs", Wiley-Interscience, New York, 1985 Examples of compounds of this class of antiinflammatory drugs include but are not limited to the following: aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketoprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, and zomepirac.

Non-steroidal cyclooxygenase inhibiting compounds can be prepared in the form of pharmaceutically acceptable salts, esters and other prodrugs. Derivative salts include relatively non-toxic inorganic or organic acid addition salts or alkaline earth metal salts of the therapeutic compounds, which can be prepared in situ during the final isolation and purification of the compounds or by separately reacting the free base with a suitable organic or inorganic acid. Where the compounds include a basic functionality such as amine or alkylamine, representative salts include hydrochloride, sulfate, acetate, maleate, lauryl sulphate, and the like. Where an acidic functionality is present, salts such as sodium, calcium, potassium and magnesium salts may be formed.

The phrase "NSAI agent" as used herein is intended to mean any non-narcotic analgesic/non-steroidal anti-inflammatory compound useful as a cyclooxygenase inhibitor, including but not limited to the derivatives of (1) propionic acid, (2) acetic acid derivatives, (3) fenamic acid, (4) biphenylcarboxylic acid and (5) oxicams.

While some of these agents are primarily used at the present time as anti-inflammatory agents and others are primarily used as analgesics, in fact it is believed that all of the contemplated compounds have both analgesic and anti-inflammatory activity and can be used at appropriate dosage levels for either purpose in various compositions.

The compounds in groups (1) through (4) typically contain a carboxylic acid function; however, those acids are sometimes administered in the form of their pharmaceutically acceptable acid addition or alkali metal salts, e.g., sodium salts.

The propionic acid derivatives include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alimoprofen, tiaprofenic acid, fluprofen and bucloxic acid. Structurally related propionic acid derivatives having similar analgesic and anti-inflammatory properties are also intended to be encompassed by this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$), typically attached directly or via a carbonyl function to a ring system, preferably to an aromatic ring system.

The acetic acid derivatives as defined herein include, but are not limited to, indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g., —CH$_2$COO$^-$Na$^+$), typically attached directly to a ring system, preferably to an aromatic or heteroaromatic ring system.

The fenamic acid derivatives as defined herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivative" as defined herein are non-narcotic analgesics/non-steroidal anti-inflammatory drugs which contain the basic structure

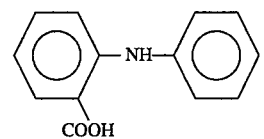

which can bear a variety of substituents and in which the free —COOH group can be in the form of a pharmaceutically acceptable salt group, e.g., —COO$^-$NA$^+$.

The biphenylcarboxylic acid derivatives as defined herein include, but are not limited to, diflunisal and flufenisal. Structurally related biphenylcarboxylic acid derivatives having similar analgesic and anti-inflammatory properties are also intended to be encompassed by this group.

Thus, "biphenylcarboxylic acid derivative" as defined herein are non-narcotic analgesics/non-steroidal anti-inflammatory drugs which contain the basic structure

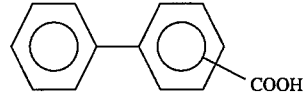

which can bear a variety of substituents and in which the free —COOH group can be in the form of a pharmaceutically acceptable salt group, e.g., —COO$^-$NA$^+$.

The oxicams as defined herein include, but are not limited to, piroxicam, sudoxicam, isoxicam, and CP-14,304. Structurally related oxicams having similar analgesic and anti-inflammatory properties are also intended to be encompassed by this group. A preferred member of this group is piroxicam.

Thus, "oxicams" as defined herein are non-narcotic analgesics/non-steroidal anti-inflammatory drugs which have the general formula

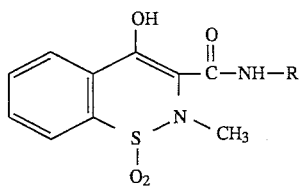

wherein R is an aryl or heteroaryl ring system.

Also included within the non-steroidal cyclooxygenase inhibitors or NSAI agents of the present invention are inhibitors as described by Flach, "Cyclooxygenase Inhibitors in Ophthalmology," Survey of Ophthalmology; Vol. 36, No. 4, (Jan.–Feb. 1992). Cyclooxygenase inhibitors are also non-steroidal antiinflammatory drugs that have become available as ophthalmic eyedrops for treatment of inflammation. These inhibitors may be grouped into six different classes: salicylates, fenamates, indoles, phenylalkanoic acids and pyrazolones. Specific drugs within the respective groups are summarized below.

| Cyclooxygenase Inhibitors | |
|---|---|
| Chemical Class | Generic Name |
| Salicylates | Aspirin, Salicylic Acid, Diflunisol |
| Indoles | Indomethacin, Sulinda, Tolmetin |
| Phenylalkanoic acids | Fenoprofen, Flurbiprofen, Ibuprofen, Ketoprofen, Ketorolac, Naproxen, Piroxicam, Suprofen |
| Phenylacetic acids | Diclofenac |
| Pyrazolons | Oxyphenbutazone, Phenylbutazone, Antipyrine, Aminopyrine, Azapropazone |

The precise type of and amount of NSAI agent or non-steroidal cyclooxygenase or other eicosanoid inhibitor for use in the present compositions will vary depending, for example, on the specific drug chosen, the dosage form thereof, i.e., standard versus sustained release, the condition for which the drug is administered and the size and kind of the organism treated.

It is within the ability of those skilled in the art to determine, upon reading this disclosure, which of the foregoing cyclooxygenase inhibiting agents will function to prevent an increase of IOP or actually decrease IOP associated with steroid, corticosteroid or glucocorticoid treatment. Preferably, those compounds of the present invention include all non-steroidal cyclooxygenase inhibitors which provide a reduction in or prevention of enhanced IOP induced by glucocorticoid treatment when used in an amount sufficient to provide a concentration of $1 \times 10^{-5}$M or less, preferably an amount of about $1 \times 10^{-9}$M to about $1 \times 10^{-5}$M, more preferably about $1 \times 10^{-8}$M to about $1 \times 10^{-6}$M in the aqueous or treated tissue of the eye.

By formulating the above-described therapeutic agents into an appropriate inert vehicle or carrier, it is possible to reduce or treat elevated intraocular pressure associated with steroid, corticosteroid or glucocorticoid treatment. In order to maintain an adequate therapeutic level of drug in the eye, the present invention also contemplates the treatment of an ophthalmic disease by administration of an opthalmically effective amount of the non-steroidal cyclooxygenase inhibiting agents of the present invention (including salts, hydrates, or solvates), in a suitable carrier, by oral, intramuscular and intravenous routes, in addition to the convenient topical route or by intraocular injection.

In general, ophthalmic formulations suitable for topical and intraocular administration may be formulated and administered in accordance with techniques known to persons skilled in the art. The formulations are preferably prepared in an anaerobic environment by making all formulations under an inert gas. The finished formulations are preferably stored in opaque or brown containers to protect them from light exposure, and under an inert atmosphere.

Aqueous polymeric solutions, aqueous suspensions, ointments, and gels are preferably used for topical formulations. The aqueous formulations may also contain liposomes for creating a reservoir of dissolved therapeutic agent. Particularly preferred among topical formulations are gels, which enhance pre-corneal retention without the inconvenience and impairment of vision associated with ointments.

Topical ophthalmic or other topical formulations should generally include between 0.001 and 10% by weight, preferably between 0.05 and 1% by weight and most preferably 0.05 and 0.6% by weight, of the therapeutic agent in a suitable polymeric carrier. Other preferred formulations contain between 0.001 to 0.009% by weight of the therapeutic agent. As will be appreciated by those skilled in the art, the amounts of non-steroidal agent needed to reduce IOP associated with steroid treatments include those amounts which will not effectively reduce inflammation, i.e., amounts lower than currently used in topical antiinflammatory formulations.

Suitable polymeric carriers include lightly crosslinked carboxy-containing polymers (such as polycarbophil), dextran, cellulose derivatives, polyethyleneglycol 400 and other polymeric demulcents.

A preferred system includes lightly crosslinked polymers of acrylic acid or the like, which are well known in the art. In a preferred embodiment, such polymers are ones prepared from at least about 90%, and preferably from about 95% to about 99.9% by weight, based on the total weight of monomers present, of one or more carboxyl-containing monoethylenically unsaturated monomers. Acrylic acid is the preferred carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers are crosslinked by using a small percentage, i.e., from about 0.01% to about 5%, and preferably from about 0.1% to about 2%, based on the total weight of monomers present, of a polyfunctional crosslinking agent. Included among such crosslinking agents are non-polyalkenyl polyether difunctional crosslinking monomers such as divinyl glycol; 2,3-dihydroxyhexa-1,5-diene; 2,5-dimethyl-1,5-hexadeone; divinylbenzene; N,N-diallylacrylamide; N,N-diallylmethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown, U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al., U.S. Pat. Nos. 4,192,827 and 4,136,250.

The lightly crosslinked polymers can of course be made from a carboxyl-containing monomer or monomers as the sole monoethylenically unsaturated monomer present, together with a crosslinking agent or agents. They can also be polymers in which up to about 40%, and preferably from about 0% to about 20% by weight, of the carboxyl containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al., U.S. Pat. No. 4,548,990 for a more extensive listing of such additional monoethylenically unsaturated monomers. Particularly preferred polymers are lightly crosslinked acrylic acid polymers wherein the crosslinking monomer is 2,3-dihydroxyhexa-1,5-diene or 2,3-dimethylhexa-1,5-diene.

The lightly crosslinked polymers used in practicing this invention are preferably prepared by suspension or emulsion polymerizing the monomers, using conventional free radical polymerization catalysts, to a dry particle size of not more than about 50 µm in equivalent spherical diameter; e.g., to provide dry polymer particles ranging in size from about 1 to about 30 µm, and preferably from about 3 to about 20 µm, in equivalent spherical diameter. In general, such polymers will range in molecular weight estimated to be greater than 2,000,000.

Aqueous suspensions formulated in accordance with this invention containing polymer particles prepared by suspension or emulsion polymerization whose dry particle size is appreciably larger than about 50 µm in equivalent spherical diameter are less comfortable when administered to the eye than suspensions otherwise identical in composition containing polymer particles whose equivalent spherical diameters are, on the average, below about 50 µm. Lightly crosslinked polymers of acrylic acid or the like prepared to a dry particle size appreciably larger than about 50 µm in equivalent spherical diameter and then reduced in size, e.g., by mechanically milling or grinding, to a dry particle size of not more than about 50 µm in equivalent spherical diameter do not work as well as polymers made from aqueous suspensions. One possible explanation for the difference of such mechanically milled or ground polymer particles as the sole particulate polymer present is that grinding disrupts the spatial geometry or configuration of the larger than 50 µm lightly crosslinked polymer particles, perhaps by removing uncrosslinked branches from polymer chains, by producing particles having sharp edges or protrusions, or by producing ordinarily too broad a range of particle sizes to afford satisfactory delivery system performance. A broad distribution of particle sizes will impair the viscosity-gelation relationship. In any event, such mechanically reduced particles are less easily hydratable in aqueous suspension than particles prepared to the appropriate size by suspension or emulsion polymerization, and also are less able to gel in the eye under the influence of tear fluid to a sufficient extent and are less comfortable once gelled than gels produced in the eye using the aqueous suspensions of this invention. However, up to about 40% by weight, e.g., from about 0% to over 20% by weight, based on the total weight of lightly crosslinked particles present, of such milled or ground polymer particles can be admixed with solution or emulsion polymerized polymer particles having dry particle diameters of not more than about 50 µm when practicing this invention. Such mixtures will also provide satisfactory viscosity levels in the ophthalmic medicament delivery systems with ease and comfort of administration and satisfactory sustained release of the medicament to the eye, particularly when such milled or ground polymer particles, in dry form, average from about 0.01 to about 30 µm, and preferably from about 1 to about 10 µm, in equivalent spherical diameter.

In the most preferred embodiment of the invention, the particles have a narrow particle size distribution. The use of a monodisperse particle will give maximum viscosity and an increased eye residence time of the ophthalmic medicament delivery systems for a given particle size. Monodisperse particles having a particle size of 30 µm and below are most preferred. Good particle packing is aided by a narrow particle size distribution.

The particles are not only subject to the upper size limits described above, but also to a narrow particle size distribution. Such use of a monodispersion of particles, which aids in good particle packing, yields a maximum increased viscosity upon contact of the suspension with the tears and increases eye residence time. At least about 80%, more preferably at least about 90% and most preferably at least about 95%, of the particles should be within a no more than about 10 µm band of major particle size distribution, and overall (i.e., considering particles both within and outside such band) there should be no more than about 20%, preferably no more than about 10% and most preferably no more than about 5% fines (i.e., particles of a size below 1 µm). It is also preferred that as the average particle size is lowered from the upper limit of 50 µm, more preferably 30 µm, to lower sizes such as 6 µm, that the band of major particle distribution be also narrowed, for example to 5 µm. Preferred sizes for particles within the band of major particle distribution are less than about 30 µm, more preferably less than about 20 µm, most preferably from about 1 µm to about 5 µm.

The aqueous suspensions of this invention may preferably contain amounts of lightly crosslinked polymer particles ranging from about 0.1% to about 6.5% by weight, and preferably from about 0.5% to about 4.5% by weight, based on the total weight of the aqueous suspension. They will preferably be prepared using pure, sterile water, preferably deionized or distilled, having no physiologically or ophthalmologically harmful constituents, and will be adjusted to a neutral pH of about 7.0 to about 7.4 using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylamino-methane), or the like and salts and buffers such as citrate/dextrose, sodium bicarbonate, ammonium chloride and mixtures of the aforementioned acids and bases.

When formulating the aqueous suspensions of this invention, their osmotic pressure (π) will be adjusted to from about 10 milliosmolar (mOsM) to about 400 mOsM, and preferably from about 100 to about 250 mOsM, using appropriate amounts of physiologically and ophthalmologically acceptable salts. Sodium chloride is preferred to approximate physiologic fluid, and amounts of sodium chloride ranging from about 0.01% to about 1% by weight and preferably from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like can also be used in addition to or instead of sodium chloride to achieve osmolalities within the above-stated ranges.

The amounts of lightly crosslinked polymer particles, the pH, and the osmotic pressure chosen from within the above-stated ranges will be correlated to give aqueous suspensions preferably having viscosities ranging from about 1,000 to about 30,000 centipoise, and preferably from about 5,000 to about 30,000 centipoise, as measured at room temperature (about 25° C.) using a Brookfield Digital LVT Viscometer equipped with a number 25 spindle and a 13R small sample adapter at 12 rpm. Higher viscosities may also be employed, and formulations of less than 100,000 centipoise can be administered as a ribbon.

The viscous gels that result from fluid eyedrops delivered by means of the aqueous suspensions of this invention have residence times in the eye ranging from about 2 to about 12 hours, e.g., from about 3 to about 6 hours. The medicaments contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present. Preferably, the aqueous suspensions provide a sustained concentration of cyclooxygenase inhibitor of between $10^{-8}$ and $10^{-6}$M, and more preferably between $10^{-7}$ and $10^{-5}$M, in the aqueous or treated tissue of the eye for at least two hours, preferably at least three hours.

The aqueous suspension topical ophthalmic medicament delivery systems of this invention can be formulated in any of several preserved or nonpreserved ways. For example the drug, the lightly crosslinked polymer particles, and the osmolality-adjusting salt can be pre-blended in dry form, added to all or part of the water, and stirred vigorously until apparent polymer dispersion is complete, as evidenced by the absence of visible polymer aggregates. Sufficient pH adjusting agent is then added incrementally to reach the desired pH, and more water to reach 100 percent formula weight can be added at this time, if necessary. Another convenient method involves adding the drug to about 95 percent of the final water volume and stirring for a sufficient time to saturate the solution. Solution saturation can be determined in known manner, e.g., using a spectrophotometer. The lightly crosslinked polymer particles and the osmolality-adjusting salt are first blended in dry form and then added to the drug-saturated suspension and stirred until apparent polymer hydration is complete. Following the incremental addition of sufficient pH adjusting agent to reach the desired pH, the remainder of the water is added, with stirring, to bring the suspension to 100 percent formula weight.

These aqueous suspensions can be packaged in preservative-free, single-dose non-reclosable containers. This permits a single dose of the medicament to be delivered to the eye one drop at a time, with the container then being discarded after use. Such containers eliminate the potential for preservative-related irritation and sensitization of the corneal epithelium, as has been observed to occur particularly from ophthalmic medicaments containing mercurial preservatives. Multiple-dose containers can also be used, if desired, particularly since the relatively low viscosities of the aqueous suspensions of this invention permit constant, accurate dosages to be administered dropwise to the eye as many times each day as necessary. In those suspensions where preservatives are to be included, suitable preservatives are chlorobutanol, Polyquat, benzalkonium chloride, cetyl bromide, and the like.

Other additives which are desirably included in the topical formulations include sodium chloride, EDTA (disodium edetate), surfactants, and preservatives like BAK (benzalkonium chloride). Administration of the formulation to the eye will typically be carried out between one and four times a day, depending on the particular problem being treated.

Formulations suitable for ocular injection fall into two categories. For subconjunctival injection, the formulations should generally include between 0.001 and 5% by weight, preferably between 0.01 and 1% by weight of therapeutic agent. Any suitable carriers may be employed, preferably polymeric carriers such as dextran or polysorbate 80. Other additives which desirably may be included in the formulations are disodium edetate and sodium sulfite. To administer the formulations to the eye, the drug formulations will be slowly injected into the bulbar conjunctiva of the eye.

For intracameral or intravitreal injections, the suitable formulation should include phosphate buffered saline, citrate buffered saline, chondroitin sulfate, or a polymeric carrier such as sodium hyaluronate (or hyaluronic acid), purified polyacrylamide or polysorbate 80. Other additives which are desirably included in the ocularly injectable formulations are sodium chloride, sodium hydroxide and hydrogen chloride, where sodium hydroxide and hydrogen chloride are used for adjustment of pH. Typically, the formulations contain between 0.001 and 1%, preferably between 0.01 and 1.0% especially when in solution, by weight of the agent.

When the agent is substantially in solution, it is rapidly available to exert its therapeutic function and lower concentrations may therefore be administered to achieve effective levels without causing tissue intolerance. When the agent is substantially in suspension, higher concentrations may be administered to achieve a sustained effective level, again without causing tissue intolerance. Hence, with solutions, lower concentrations are employed to avoid local tissue damage. With a suspension, higher concentrations are employed because a smaller dissolved amount is introduced for immediate activity.

To administer the formulations intravitreally to the eye, the drug formulation will be injected through the sclera layer of the eye into the vitreous cavity. To administer the formulations intracamerally, the drug formulations will be injected through the cornea into the anterior chamber of the eye.

Formulations for intravenous, intramuscular, and oral administration are likewise prepared in accordance with techniques well known to persons skilled in the art. Intravenous formulations for ophthalmic use in methods of the present invention may be prior art formulations used for other purposes and will typically include between 0.01 and 50.0% by weight and preferably between 1.0 and 10.0% by weight of the therapeutic agent. Suitable carriers for such NSAI agents are those well known to persons skilled in the art such as citrate buffer, borate buffer and others. Other additives which may be desirably added to intravenous formulations include sodium chloride, sodium sulfite, disodium edetate and benzyl alcohol. Alternative formulations suitable for intravenous administration include carriers such as lipid emulsions containing the therapeutic agent. To administer the intravenous formulations for treatment of the eye, the drug formulations are preferably dose injected or infused into a major vein (e.g., in the arm area), or introduced by continuous intravenous drip.

Intramuscular formulations will typically include between 0.01 and 10.0% by weight and preferably between 0.5 and 5.0% by weight of the therapeutic agent. Suitable adjuvants in aqueous solution or suspension for intramuscular lazaroid formulations are those well known to persons skilled in the art such as polysorbate 80, methyl cellulose, and other demulcents. Other additives desirably added to intramuscular formulations include sodium chloride and sodium bisulfite. To administer the intramuscular formulations for treatment of the eye, the drug formulations will be injected for example into the upper outer quadrant of the gluteal muscle.

Formulations suitable for oral administration will include both liquid formulations (aqueous solutions, aqueous suspension, elixirs, and the like) and solid dosage forms, both containing additives and adjuvants well known to persons skilled in the art. Aqueous solutions and suspensions for liquid oral administration will typically contain between 0.05 and 50% by weight and preferably between 1.0 and 10.0% by weight of the NSAI agent. Suitable adjuvants may be used as carriers to provide wetability and stability such as propylene glycol, lightly crosslinked carboxy-containing polymers such as polycarbophil, ethyl cellulose, hydroxypropyl cellulose and methyl cellulose. Other additives, including sodium edetate, methyl and propyl parabens, flavoring agents and colorants may be employed if desirable. Solid dosage forms for oral administration may also be prepared as capsules, caplets or tablets with the aid of fillers, lubricants and stabilizers. To administer oral formulations for treatment of the eye, the drug is swallowed in solid dosage form or as a solution or suspension.

Studies of human trabecular meshwork (HTM) cells grown in tissue culture in which biochemical and morphological responses have been evaluated have provided a model system to evaluate the mechanisms for the development of steroid effects to raise IOP, and provide a means to investigate new therapeutic approaches. Under appropriate cell culture conditions, HTM cells may be propagated using sufficiently high split ratios to obtain populations of these cells at early passages for reproducible experimental evaluations. In vitro studies of confluent, stable monolayers of HTM cells reveal a variety of structural and functional properties of the trabecular meshwork cell type which appear important for normal maintenance of the aqueous humor outflow pathway. Using these cells, it is possible to consider alterations produced by steroids and other drugs that may be related to effects on intraocular pressure (IOP).

Investigations of HTM cells with topical glucocorticoid treatment proved that steroids such as dexamethasone produced major new protein inductions in HTM cells which became progressively more noticeable between 1 and 3 weeks of 100 nM dexamethasone exposure. The correlation between dexamethasone effects on these protein inductions and the clinically observed rise in IOP suggested that prolonged glucocorticoid treatments on HTM cells provide a model system to study steroid effects on outflow facility, as described in Polansky et al., "Glucocorticoid regulation of cultured human trabecular cells: a model system to study effects of steroids on IOP," Invest Ophthalmol Vis Sci 26:5 (1985). Studies of the HTM model system have reported that inductions of protein/glycoproteins in the molecular weight range of about 54–56 kDa (glucocorticoid-induced protein at 55 kDa, termed GIP-55 in the above-cited publication) and about 65–67 kDa (glucocorticoid-induced protein at 66 kDa, termed GIP-66 in the above-cited publication) were found in cytosol and media fractions, respectively, of dexamethasone treated HTM cultures. Thus, these proteins/glycoproteins provide a suitable marker for steroid induced elevated IOP since these inductions were not observed in the non-treated controls evaluated in this study. As mentioned above, these markers are referred to herein as 55 kDa and 66 kDa protein/glycoprotein marker inductions but, of course, as will be appreciated by those skilled in the art, the actual molecular weight of the protein according to the methods described herein, i.e., gel electrophoresis, is within a range of the recited values and when referred to herein such marker induction should include the major induction within the range.

Using the above models, it has now unexpectedly been found that the non-steroidal cyclooxygenase inhibiting agents or NSAI agents of the present invention do not induce, or induce to a minimal extent, the protein markers for elevated IOP in the model system. In fact, it has unexpectedly been found that conjoint treatment of steroids and NSAI agents provides protein/glycoprotein marker reduction and, thus, would be expected to help minimize or prevent the elevated IOP found with steroid treatment.

According to preferred embodiments of the invention, the cyclooxygenase inhibiting agents or NSAI agents of the present invention provide a protein/glycoprotein marker reduction of steroid induced glycoprotein markers, i.e., either 55 kDA or 66 kDa proteins, where the marker reduction equals $$\frac{\text{induction of glycoprotein with steroid treatment alone} - \text{induction of glycoprotein with combination of steroid and non-steroid treatment}}{\text{induction of glycoprotein with steroid treatment alone}} \times 100\%$$

Of course, steroid induced elevated IOP may also be subsequently treated using the non-steroidal cyclooxygenase agents of the present invention. In such case, the agent may be applied to reduce elevated IOP. In this case, the marker reduction equals $$\frac{\text{induction of glycoprotein with steroid treatment alone} - \text{induction of glycoprotein after treatment with non-steroidal agent}}{\text{induction of glycoprotein with steroid treatment alone}} \times 100\%$$

Most preferably, the non-steroidal inhibiting agents or NSAI agents used in the methods and compositions of the present invention are used in an amount sufficient to provide a protein marker reduction of at least about 5%, more preferably at least about 10%, even more preferably at least about 20% and most preferably at least about 40%. Of course, the amount of protein marker reduction depends on the type and amount of non-steroidal cyclooxygenase inhibiting agent or NSAI agent used.

In view of the above, the non-steroidal cyclooxygenase inhibiting agents or NSAI agents used in the methods and compositions of the present invention are used in an amount sufficient to provide reduced IOP by at least about 5%, more preferably at least about 10%, even more preferably at least about 20%, and even more preferably at least about 40%. Again, however, the amount of IOP reduction depends on the amount and type of non-steroidal cyclooxygenase inhibiting agent or NSAI agent used.

In order to evaluate the effects of glucocorticoids and non-steroidal cyclooxygenase inhibitors on the eye, cell cultures of human trabecular meshwork cells are studied. A discussion of how such cell cultures are prepared and evaluated is set forth below.

Cell Culture and Cell Growth Experiments

Human trabecular meshwork (HTM) cells are used for the experiments described below. The HTM cells are prepared as described in Polansky et al., Trabecular meshwork cell culture in glaucoma research, Ophthalmology, 1984; 91: 580–595; Polansky et al., Human trabecular cells I: Establishment in tissue culture and growth characteristics, Invest Ophthalmol Vis Sci, 1979; 18:1043–1049; Alvarado et al., Humban trabecular cells II: Ultrastructural characteristics of cultured trabecular cells, Invest Ophthalmol Vis Sci, 1982; 23:464–478; and Polansky et al., Studies on human trabecular cells propagated in vitro, Vision Res, 1981; 21:155, each of which are hereby incorporated by reference.

To perform the experiments described below, third to fifth passage HTM cultures are removed from cryopreserved stocks, plated at approximately 10,000 cells/cm$^2$, and grown seven to ten days post-confluency in Dulbecco's modified Eagle's (DME) medium with 10% fetal calf serum (FCS) to obtain stable endothelial-like monolayers. The protein synthesis studies presented below are performed on these stable HTM monolayer cultures.

The glucocorticoid effects on HTM cell division are evaluated on growing cultures using DME medium with 10% FCS. Glucocorticoid and non-steroidal cyclooxygenase inhibiting agent treatments begun the day after HTM cells are plated at 2,500 cells/cm$^2$. Effects are measured during log phase of growth (7 days) and after the control cultures reaches confluency (which varies between 3 to 6 weeks, depending on the HTM cell line and the serum in the culture medium).

The ability of non-steroidal cyclooxygenase inhibiting agents to influence glucocorticoid effects are evaluated by addition of the non-steroidal cyclooxygenase inhibiting agents in the desired concentration when treating the HTM cell cultures with the glucocorticoid, i.e., dexamethasone. Various agents are compared at various concentrations as described below.

Evaluation of Non-steroidal Cyclooxygenase Inhibiting Agents for their Effects on Glucocorticoid Induced Changes in HTM Cell Specific Protein Synthesis Glucocorticoid and non-steroidal cyclooxygenase inhibiting agent effects on specific protein/glycoprotein synthesis are evaluated by addition of [$^{35}$S] methionine to label newly synthesized proteins in the HTM cells. Confluent cultures which have been exposed to the glucocorticoid (dexamethasone) and non-steroidal cyclooxygenase inhibiting agent for varying times (media changes 24 hours prior to labelling) are placed into methionine-free medium with 100–500 μCi [$^{35}$S]-methionine per ml media (New England Nuclear; specific activity 1100 ci/mmol, 10% FCS and the appropriate concentration of dexamethasone and/or inhibiting agent. Dexamethasone inductions in the cytosol are evaluated 15 to 60 minutes after addition of [$^{35}$S] methionine (short labeling times providing an estimate of protein synthetic rates). Proteins/glycoproteins present in the HTM tissue culture medium are from 2 hour serum-free DME collection after a 3 hour initial cell labeling as described above. Pulse-chase experiments are also performed which helps in the choice of these conditions.

Immediately after collection, each sample of cytosol proteins is exposed to lysis buffer (20 mM Tris HCl, pH 7.6; 10 mM MgSO4; 0.1% TX100; chymostatin, 2 μg/ml; leupeptin, 4 μg/ml; bacitracin, 25μ/ml; PMSF, 1 mM) at 4° C. The trichloroacetic acid precipitable counts of the cell lysates are used to normalize the amounts of lysate or media added to the gel electrophoresis lanes. The samples are diluted according to TCA assay results and gel buffer is added to a final concentration of 10% glycerol, 2% SDS, 5% beta-Mercaptoethanol, and 62.5 mM Tris, pH 6.8. Samples are then boiled for 2 minutes, cooled, spun and loaded onto gels.

Neuraminidase Digestions and Tunicamycin Treatments

To evaluate the possibility of sialic acid residues on the major glycoprotein induction in the dexamethasone treated HTM cultures, two hour media collections of secreted proteins are performed as described above. Enzyme digestions using Neuraminidase Type X N2133 (affinity purified from *Clostridium perfringes*, Sigma, St. Louis) are conducted according to Schwartz et al., Characterization of the sialoglycoprotein receptor in a continuous hepatoma line, J. Biol Clem, 1981; 256: 8878–888, which is hereby incorporated by reference. Samples are prepared using 0.1M sodium acetate buffer containing 1 mg/ml human serum albumin, 0.2% NAN$_3$, pH5 and incubated with neuraminidase (0.05 U/ul) for 5 hours at 37° C. The reactions are stopped by boiling the samples, with all further preparation for electrophoresis performed on ice. Tunicamycin effects on the secreted HTM proteins/glycoproteins are evaluated by placing dexamethasone treated (300 nM) cultures into methionine-free medium with 10% FCS containing tunicamycin (1–6 μg/ml). The labeled lysate and media proteins are collected and the TCA-precipitable counts are determined as described above.

Phosphorimager Quantitation and Gel Electrophoresis

Previously published methods involving computerized spot matching (PDQuest) programs on three different autoradiogram exposures of large format 2-D gels according to Polansky et al., Eicosanoid production and glucocorticoid regulator mechanisms in cultured human trabecular meshwork cells, Prog. Clin Biol Res, 1989; 312:113–138, which is hereby incorporated by reference, are used to quantitate dexamethasone effects on specific protein synthesis in the HTM cultures. Phosphorimager quantitations, greatly reduces the time and cost of obtaining dose-response and time-course data in different HTM lines. This method is primarily useful in evaluating glucocorticoid effects on secreted proteins/glycoproteins in HTM cells because of the relatively few secreted proteins and the large size of the dexamethasone inductions of interest. For the studies shown here, a discontinuous buffer system is 11% acrylamide, pH 8.8. Gels are run for approximately five hours at a constant current (30 mA/gel) in a running buffer consisting of 25 mM Tris, 192 mM Glycine, and 0.1% SDS. Gels are stained in a solution consisting of 0.5% Coomassie R-250, 50% ethanol, and 10% acetic acid for 30 minutes and then destained, first in 40% ethanol/10% acetic acid, then in 10% ethanol/ 5% acetic acid for one hour per bath. Destained gels are then soaked in deionized water for 30 minutes and dried on Whatman 3 mm under vacuum at 60° C. Dried gels are then pressed flat overnight before exposure to a Phosphorimager screen (Phosphor Screen, Molecular Dynamics, Sunnyvale, Calif.) at room temperature, or standard x-ray film at −70° C. to visualize the labeled protein bands. The phosphor screens require approximately 10% of the time necessary for an autoradiogram exposure using x-ray film. For quantitation, the screens are scanned using a Phosphorimager model 400E, with gel files stored on a magneto-optical disk. Analyses are performed using the Image Quant v.3.22 software package, which allow the quantitation of radiolabeled protein bands over a four log-unit range of intensity. This method overcomes the substantial problems involved in obtaining quantitative information from densitometry of standard autoradiograms, which must have internal standards, at least three x-ray exposures, and difficult computer software to overcome the non-linearity of the film.

Results

Table 1 below provides the area integration in units of Phosphorimager counts (i.e. pixel values, which is directly related to $^{35}S$-methionine incorporation) in the samples for the 66 kDa protein/glycoprotein marker induction used as a marker in the media and for the 55 kDa protein/glycoprotein marker induction used as a marker in the cell.

TABLE 1

Glycoprotein Induction Responses Using Dexamethasone and Combinations of Dexamethasone and NSAI Agents[1]

| Treatment | Concentration of Dexamethasone (M) | Concentration of NSAI (M) | Induction of 55 kDa Protein | Induction of 66 kDa Protein |
|---|---|---|---|---|
| Dexamethasone | $1 \times 10^{-6}$ | 0 | 24,297 | 30,712 |
| Dexamethasone & Diclofenac | $1 \times 10^{-6}$ | $(1 \times 10^{-9})$ | 23,704 | 28,062 |
| Dexamethasone & Diclofenac | $1 \times 10^{-6}$ | $(1 \times 10^{-8})$ | 21,963 | 24,468 |
| Dexamethasone & Diclofenac | $1 \times 10^{-6}$ | $(1 \times 10^{-7})$ | 19,540 | 21,645 |
| Dexamethasone & Diclofenac | $1 \times 10^{-6}$ | $(1 \times 10^{-6})$ | 19,374 | 17,885 |
| Dexamethasone & Indomethacin | $1 \times 10^{-6}$ | $(1 \times 10^{-7})$ | — | 21,562 |
| Dexamethasone & Indomethacin | $1 \times 10^{-6}$ | $(1 \times 10^{-6})$ | — | 24,025 |
| Dexamethasone & Flurbiprofen | $1 \times 10^{-6}$ | $(1 \times 10^{-7})$ | — | 30,674 |
| Dexamethasone & Flurbiprofen | $1 \times 10^{-6}$ | $(1 \times 10^{-6})$ | — | 26,109 |
| Dexamethasone & Fenoprofen | $1 \times 10^{-6}$ | $(1 \times 10^{-7})$ | — | 29,342 |
| Dexamethasone & Fenoprofen | $1 \times 10^{-6}$ | $(1 \times 10^{-6})$ | — | 21,903 |
| Dexamethasone & Ibuprofen | $1 \times 10^{-6}$ | $(1 \times 10^{-7})$ | — | 32,908 |
| Dexamethasone & Ibuprofen | $1 \times 10^{-6}$ | $(1 \times 10^{-6})$ | — | 29,413 |
| Dexamethasone & Aspirin | $1 \times 10^{-6}$ | $(1 \times 10^{-6})$ | — | 31,197 |
| Dexamethasone & Aspirin | $1 \times 10^{-6}$ | $(1 \times 10^{-5})$ | — | 25,766 |

[1]Induction responses not corrected for Background.

As indicated above, the use of certain NSAI agents in proper concentrations reduces the protein/glycoprotein induction (marker) significantly, whereas others do not. Of course, in view of the above, those skilled in the art will be able to readily determine the appropriate NSAI agent and concentration needed.

Preparation of Preferred Topical Formulations

A hydrated polymeric dispersion is prepared by slowly dispersing 1.0 part of Noveon™ AA-1 type acrylic polymer, available from B.F Goodrich, into a beaker fitted with an overhead stirrer containing two-thirds of the final deionized water content and stirring for one hour. Then, 0.10 parts of edetate disodium is added to the dispersion followed by stirring for 10 minutes. The resulting dispersion possessing a pH of about 3.0–3.5 is sterilized by autoclaving at 121° C. for 20 minutes. Diclofenac sodium frequently used in the treatment of ocular inflammation is dissolved separately in approximately one-fifth of the final weight of water, added to the polymer mixture by sterile filtration (0.22 μm filter) and stirred for 10 minutes. The mixture is adjusted to pH 7.2 with 10N sodium hydroxide, brought to final weight with water by sterile filtration and aseptically filled into unit-dose containers.

Table 2 sets forth the amounts of each component in the sample formulations.

TABLE 2

Amount of Each Component

In Sample Formulations

| INGREDIENTS | Sample 1 Weight Percent (% w/w) | Sample 2 Weight Percent (% w/w) | Sample 3 Weight Percent (% w/w) |
|---|---|---|---|
| Diclofenac Sodium | 0.01 | 0.05 | 0.1 |
| Noveon ™ -AA-1 | 1.0 | 1.0 | 1.0 |
| Edetate Disodium | 0.1 | 0.1 | 0.1 |
| Sodium Chloride | 0.7 | 0.7 | 0.7 |
| Sodium Hydroxide ION | g.s. to pH 7.2 | g.s. to pH 7.2 | g.s. to pH 7.2 |
| Purified Water | 100.0 | 100.0 | 100.0 |

The above discussion of this invention is directed primarily to preferred embodiments and practices thereof. It will be readily apparent to those skilled in the art that further changes and modifications in actual implementation of the concepts described herein can easily be made without departing from the spirit and scope of the invention as defined by the following claims.

We claim:

1. A method for preventing or treating non-inflammatory induced elevated intraocular pressure associated with administered or endogenous glucocorticoids comprising administering to a mammalian organism a composition including (a) an ophthalmologically effective amount of a non-steroidal cyclooxygenase inhibitor, and (b) a pharmaceutically acceptable carrier, to reduce or prevent an elevation of intraocular pressure induced by concurrent or previous treatment with glucocorticoids or by endogenous glucocorticoids.

2. The method according to claim 1, wherein said preventing or treating prevents or reduces an elevation of intraocular pressure induced by concurrent or previous treatment with glucocorticoids.

3. The method according to claim 2, wherein said cyclooxygenase inhibitor is selected from the group consisting of salicylates, indoles, phenylalkanoic acids, phenylacetic acids and pyrazolons.

4. The method according to claim 2, wherein said cyclooxygenase inhibitor is selected from the group consisting of diclofenac, indomethacin and fenoprofen.

5. The method according to claim 4, wherein said non-steroidal cyclooxygenase inhibitor is diclofenac.

6. The method according to claim 1, wherein said composition is administered topically in an aqueous polymeric solution, aqueous suspension, ointment or gel vehicle.

7. The method according to claim 6, wherein composition is free of preservatives.

8. The method according to claim 1, wherein said composition comprises between about 0.001 and about 10% by weight of said inhibitor.

9. The method according to claim 8, wherein said composition comprises between about 0,001 and about 0.009% by weight of said inhibitor.

10. The method according to claim 1, wherein said composition is administered to provide a concentration of said inhibitor of less than about $1\times10^{-5}$M in the aqueous humor of the eye.

11. The method according to claim 10, wherein said composition is administered to provide a concentration of said inhibitor of between about $1\times10^{-9}$M and about $1\times10^{-5}$M in the aqueous humor of the eye.

12. The method according to claim 11, wherein said composition is administered to provide a concentration of said inhibitor of between about $1\times10^{-8}$M and about $1\times10^{-6}$M in the aqueous humor of the eye.

13. The method according to claim 1, wherein said composition provides a sustained release of said inhibitor for at least two hours in a concentration of between $1\times10^{-7}$M to $1\times10^{-5}$M in the aqueous humor of the eye.

14. The method according to claim 13, wherein said composition provides a sustained release of said inhibitor for at least three hours.

15. The method according to claim 1, wherein said composition provides a sustained release of said inhibitor for at least two hours in a concentration of between $1\times10^{-8}$M to $1\times10^{-6}$M in the aqueous humor of the eye.

16. The method according to claim 15, wherein said composition provides a sustained release of said inhibitor for at least three hours.

17. The method according to claim 1, wherein said inhibitor reduces or prevents the 55 kDa protein/glycoprotein marker induction in HTM cells associated with the treatment of the eye with glucocorticoids.

18. The method according to claim 17, wherein said inhibitor provides a marker reduction of at least about 5%.

19. The method according to claim 18, wherein said inhibitor provides a marker reduction of at least about 20%.

20. The method according to claim 19, wherein said inhibitor provides a marker reduction of at least about 40%.

21. The method according to claim 1, wherein said inhibitor reduces or prevents the 66 kDa protein/glycoprotein marker induction in HTM cell media associated with the treatment of the eye with glucocorticoids.

22. The method according to claim 21, wherein said inhibitor provides a marker reduction of at least about 5%.

23. The method according to claim 22, wherein said inhibitor provides a marker reduction of at least about 20%.

24. The method according to claim 23, wherein said inhibitor provides a marker reduction of at least about 40%.

25. The method according to claim 1, wherein said composition is administered by intraocular injection.

26. The method according to claim 1, wherein said composition is administered orally.

27. The method according to claim 26, wherein the composition is administered in an aqueous solution, aqueous suspension, elixir, tablet, caplet or capsule.

28. The method according to claim 1, wherein the composition is administered by intravenous injection.

29. The method according to claim 1, further comprising reducing elevated intraocular pressure associated with treatment with glucocorticoids by at least about 10%.

30. The method according to claim 29, further comprising reducing elevated intraocular pressure associated with treatment with glucocorticoids by at least about 20%.

31. The method according to claim 30, further comprising reducing elevated intraocular pressure associated with treatment with glucocorticoids by at least about 40%.

32. The method according to claim 1, further comprising inhibiting onset or progression of primary open angle glaucoma.

33. The method according to claim 1, further comprising inhibiting onset or progression of pigmentary glaucoma.

34. A method for preventing or treating non-inflammatory induced elevated intraocular pressure associated with administered or endogenous glucocorticoids comprising administering to a mammalian organism a composition including (a) an opthalmically effective amount of a non-steroidal anti-inflammatory agent, and (b) a pharmaceutically acceptable carrier to arrest processes damaging to the eye resulting from chronic exposure of the eye to glucocorticoids.

35. The method according to claim 34, wherein said processes damaging to the eye include either 55 kDa or 66 kDa proteins/glycoproteins marker induction.

36. The method according to claim 34, wherein said pharmaceutically acceptable carrier is an aqueous polymeric solution, suspension, ointment or gel for topical formulations.

37. The method according to claim 36, wherein said pharmaceutically acceptable carrier includes a lightly cross-linked carboxy-containing polymer.

38. The method according to claim 34, wherein said non-steroidal anti-inflammatory agent is diclofenac present in said formulation in an amount from about 0.001 to about 10% by weight of the composition.

39. The method according to claim 38, wherein said diclofenac is present in said formulation in an amount from about 0.001 to about 0.009% by weight of the composition.

40. The method according to claim 34, wherein said composition is administered in an amount sufficient to provide an ophthalmically effective amount of said agent not exceeding $1\times10^{-5}$M in the aqueous humor of the eye.

41. The method according to claim 34, further comprising reducing elevated intraocular pressure associated with treatment with glucocorticoids by at least about 20%.

42. A method for preventing damage to or treating damage to human trabecular meshwork cells associated with treatment of the eye with glucocorticoids comprising administering a composition to a mammalian organism having been treated or being treated with glucocorticoids, said composition including an opthalmically effective amount of a non-steroidal anti-inflammatory agent and an inert carrier.

43. The method according to claim 42, wherein said non-steroidal anti-inflammatory agent is a cyclooxygenase inhibitor.

44. The method according to claim 43, wherein said cyclooxygenase inhibitor is selected from the group consisting of salicylates, indoles, phenylalkanoic acids, phenylacetic acids and pyrazolons.

45. The method according to claim 43, wherein said non-steroidal cyclooxygenase inhibitor is selected from the group consisting of diclofenac, indomethacin and fenoprofen.

46. The method according to claim 45, wherein said non-steroidal cyclooxygenase inhibitor is diclofenac.

47. The method according to claim 42, wherein said composition is administered topically in an aqueous polymeric solution, aqueous suspension, ointment or gel vehicle.

48. The method according to claim 42, wherein said composition comprises between about 0.001 and about 10% by weight of said inhibitor.

49. The method according to claim 42, wherein said composition comprises between about 0.001 and about 0.009% by weight of said inhibitor.

50. The method according to claim 42, wherein said composition is administered to provide a concentration of said inhibitor of less than about $1\times10^{-5}$M in the aqueous humor of the eye.

51. The method according to claim 42, wherein said composition is administered to provide a concentration of said inhibitor of between about $1\times10^{-9}$M and about $1\times10^{-5}$M in the aqueous humor of the eye.

52. The method according to claim 51, wherein said composition is administered to provide a concentration of said inhibitor of between about $1\times10^{-8}$M and about $1\times10^{-6}$M.

53. The method according to claim 42, wherein said inhibitor reduces or prevents 55 kDa protein/glycoprotein marker induction in HTM cells associated with the treatment of the eye with glucocorticoids.

54. The method according to claim 53, wherein said inhibitor provides a marker reduction of at least about 5%.

55. The method according to claim 54, wherein said inhibitor provides a marker reduction of at least about 20%.

56. The method according to claim 55, wherein said inhibitor provides a marker reduction of at least about 40%.

57. The method according to claim 42, wherein said inhibitor reduces or prevents 66 kDa protein/glycoprotein marker induction in HTM cell media associated with the treatment of the eye with glucocorticoids.

58. The method according to claim 57, wherein said inhibitor provides a marker reduction of at least about 5%.

59. The method according to claim 58, wherein said inhibitor provides a marker reduction of at least about 20%.

60. The method according to claim 59, wherein said inhibitor provides a marker reduction of at least about 40%.

61. The method according to claim 42, wherein said composition is administered by intraocular injection.

62. The method according to claim 42, wherein said composition is administered orally.

63. The method according to claim 62, wherein the composition is administered in an aqueous solution, aqueous suspension, elixir, tablet, caplet or capsule.

64. The method according to claim 42, wherein the composition is administered by intravenous injection.

65. The method according to claim 42, further comprising reducing elevated intraocular pressure associated with treatment with glucocorticoids by at least about 10%.

66. The method according to claim 58, further comprising reducing elevated intraocular pressure associated with treatment with glucocorticoids by at least about 20%.

67. The method according to claim 59, further comprising reducing elevated intraocular pressure associated with treatment with glucocorticoids by at least about 40%.

68. A composition adapted for preventing or treating non-inflammatory induced elevated intraocular pressure associated with administered or endogenous steroids comprising (a) an ophthalmically effective amount of between 0.001 and about 0.009% by weight of a non-steroidal cyclooxygenase inhibitor of a type to reduce or prevent an elevation of intraocular pressure induced by concurrent or previous treatment with glucocorticoids, and (b) a pharmaceutically acceptable carrier therefor.

69. The composition according to claim 68, wherein said non-steroidal cyclooxygenase inhibitor is a non-steroidal anti-inflammatory agent selected from the group consisting of salicylates, indoles, phenylalkanoic acids, phenylacetic acids, and pyrazolons.

70. The composition according to claim 69, wherein said cyclooxygenase inhibitor is diclofenac, indomethacin or fenoprofen.

71. The composition according to claim 70, wherein said cyclooxygenase inhibitor is diclofenac.

72. The composition according to claim 71, wherein said diclofenac is present in an amount between 0.005 to 0.008% by weight.

73. The composition according to claim 71, wherein said composition is formulated for topical ophthalmic application, and said carrier includes a lightly cross-linked carboxy-containing polymer for sustained release of said diclofenac.

74. The composition according to claim 68, wherein said composition is formulated for topical ophthalmic application, and said carrier includes a lightly cross-linked carboxy-containing polymer for sustained release of said non-steroidal cyclooxygenase inhibitor.

* * * * *